US00PP31789P2

(12) United States Plant Patent
Doezema

(10) Patent No.: US PP31,789 P2
(45) Date of Patent: May 19, 2020

(54) ***SEDUM* PLANT NAMED 'SPIRALING DOOZIE'**

(50) Latin Name: *Sedum spurium*
Varietal Denomination: Spiraling Doozie

(71) Applicant: Eric Jon Doezema, Hudsonville, MI (US)

(72) Inventor: Eric Jon Doezema, Hudsonville, MI (US)

( * ) Notice: Subject to any disclaimer, the term of this patent is extended or adjusted under 35 U.S.C. 154(b) by 0 days.

(21) Appl. No.: 16/602,076

(22) Filed: Jul. 30, 2019

(51) Int. Cl.
*A01H 5/02* (2018.01)
*A01H 6/32* (2018.01)

(52) U.S. Cl.
USPC ..... Plt./479
CPC ..... *A01H 6/32* (2018.05)

(58) Field of Classification Search
USPC ..... Plt./479
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Sedum* plant named 'Spiraling Doozie' that is characterized by its very heavy branching and branches from every leaf node along the stems, its consistent, spreading mound, ground-cover plant habit, its glossy foliage that is variegated foliage with green centers that emerge with margins that are intense gold in color and turn to creamy white in summer with light pink edges and turn back to gold in autumn.

2 Drawing Sheets

Botanical classification: *Sedum spurium.*
Variety denomination: 'Spiraling Doozie'.

BACKGROUND OF THE INVENTION

The present invention relates to a new and distinct cultivar of *Sedum* plant, botanically of hybrid origin and known as *Sedum* 'Spiraling Doozie' referred to hereinafter by its cultivar name, 'Spiraling Doozie'. The new cultivar of *Sedum* is a hardy herbaceous perennial grown for use as a landscape and container plant and is particularly suitable as a groundcover.

The Inventor discovered the new cultivar in May of 2017 as a naturally occurring branch mutation of *Sedum spurium* cultivar 'Tricolor' (not patented) growing in a 1-quart container in his greenhouse in Hudsonville, Mich.

Asexual propagation of the new cultivar was first accomplished by stem tip cuttings in August of 2017 in Hudsonville, Mich. Asexual propagation by stem tip cuttings and division has determined the characteristics to be stable and reproduced true to type in successive generations.

SUMMARY OF THE INVENTION

The following traits have been repeatedly observed and are determined to be the characteristics of the new cultivar. These attributes in combination distinguish 'Spiraling Doozie' as a unique cultivar of *Sedum.*

1. 'Spiraling Doozie' exhibits very heavy branching and branches from every leaf node along the stems.
2. 'Spiraling Doozie' exhibits a consistent, spreading mound, ground-cover plant habit.
3. 'Spiraling Doozie' exhibits glossy foliage.
4. 'Spiraling Doozie' exhibits glossy foliage that is variegated with green centers and emerge with margins that are intense gold color and turn to creamy white in summer with light pink edges and turn back to gold in autumn.

The parent plant of 'Spiraling Doozie', 'Tricolor', differs from 'Spiraling Doozie' in having variegated foliage that emerges with a heavily suffused pink color in the spring then turns to white in the summer and fall, margins that are 40% less in width and in not readily produce side branches. 'Spiraling Doozie' can be most closely compared to *Sedum spurium* 'Fool's Gold' (not patented) and a plant of *Sedum spurium variegatum* (not patented). 'Fool's Gold' is similar to 'Spiraling Doozie' in having a low-growing groundcover plant habit with an abundance of crown buds and multi-branching. 'Fool's Gold' differs from 'Spiraling Doozie' in having foliage that emerges with cream and pink margins with hot pink edges, leaves that are 30% narrower in width with less heavily serrated margins. A plant of *Sedum spurium variegatum* is similar to 'Spiraling Doozie' in having a groundcover plant habit and in having variegated foliage. *Sedum spurium variegatum* differs from 'Spiraling Doozie' in having leaves that are smaller in size with narrower margins and margin edges that are hot pink in color.

BRIEF DESCRIPTION OF THE DRAWINGS

The accompanying colored photographs illustrate the overall appearance and distinct characteristics of the new *Sedum*. The photographs were taken of a plant about 5 months in age as grown in a greenhouse in a 1-gallon container in Hudsonville, Mich.

The photograph in FIG. 1 provides a view of the plant habit and foliage coloration of 'Spiraling Doozie' in the spring.

Figure 1:
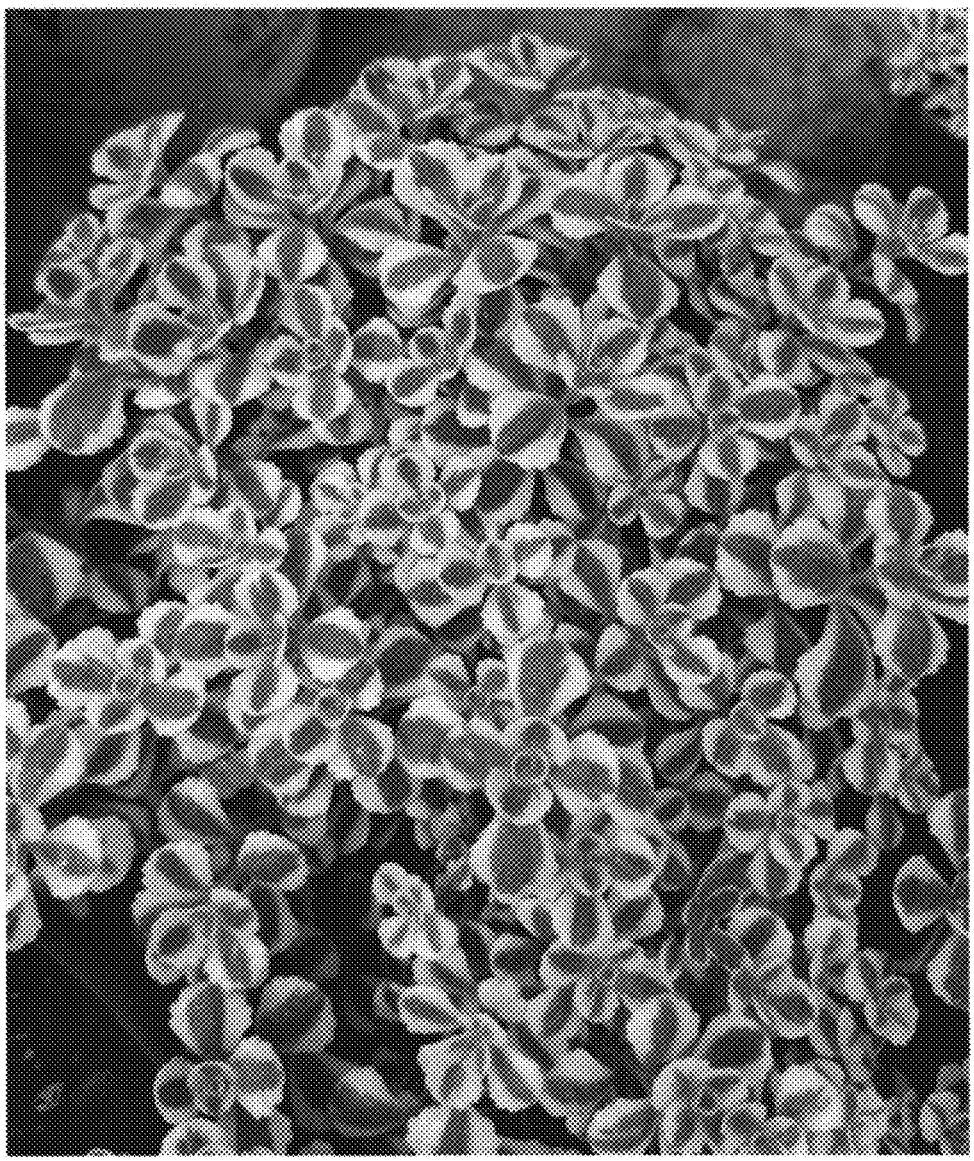
Figure 2:
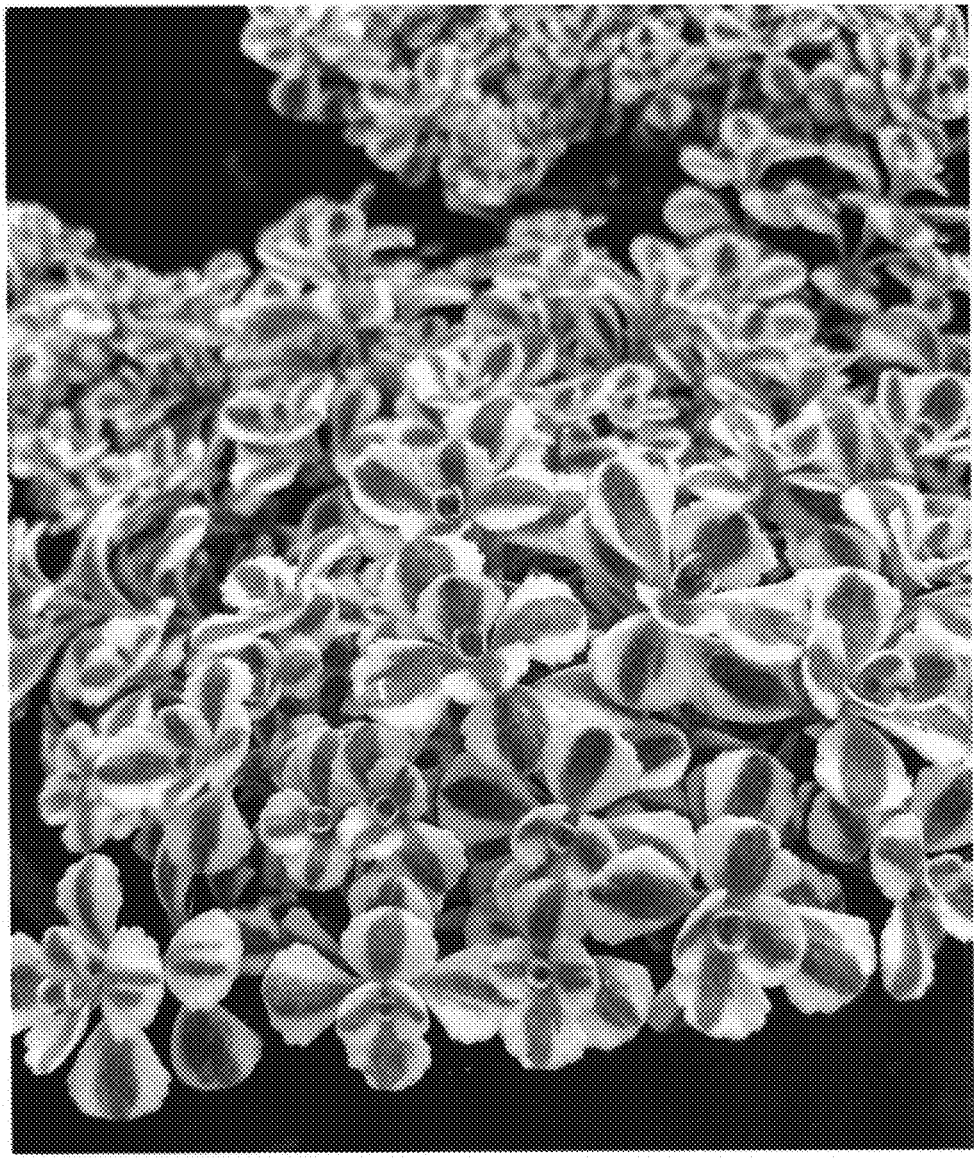

The photograph in FIG. 2 provides a view of the foliage coloration of 'Spiraling Doozie' in the summer.

The colors in the photographs may differ slightly from the color values cited in the detailed botanical description, which accurately describe the colors of the new *Sedum*.

DETAILED BOTANICAL DESCRIPTION

The following is a detailed description of the new cultivar as observed on 5-month-old plants of 'Spiraling Doozie' as grown in a greenhouse in one-gallon containers in Hudsonville, Mich. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Herbaceous perennial.

*Plant habit*.—Spreading mound, ground-cover, well-branched.

*Height and spread*.—Reaches average of 10 cm in height and about 30 cm in spread, mature plant reaches 16 cm in height and 46 cm in width.

*Hardiness*.—At least hardy in U.S.D.A. Zones 4 to 9.

*Disease and pests*.—No susceptibility or resistance to diseases or pests has been observed.

*Root description*.—Fibrous, 155A.

*Propagation*.—Tip stem cuttings.

*Growth rate*.—Vigorous.

*Rooting*.—Roots are initiated in about 15 days, a young plant can be produced in about 2 months.

Stem description:

*Stem shape*.—Rounded.

*Stem size*.—An average of 15 cm in length and 2 mm in width.

*Internode length*.—Average of 8 mm.

*Stem color*.—Young; 157A, mature; a blend of 160B, 196C and 199A.

*Stem surface*.—Young; glabrous, slightly glossy, mature; rugose, slightly glossy.

*Branching habit*.—Numerous basal branches.

Foliage description:

*Leaf shape*.—Obicular.

*Leaf division*.—Simple.

*Leaf arrangement*.—Opposite.

*Leaf base*.—Acute.

*Leaf apex*.—Broadly rounded.

*Leaf venation*.—Not conspicuous, color matches leaf color.

*Leaf margins*.—Undulate.

*Leaf attachment*.—Petiolate.

*Leaf orientation*.—Nearly horizontal to slightly upward, slightly cupped.

*Leaf texture*.—Thick, succulent.

*Leaf surface*.—Both surfaces dull, satiny, margins sparsely covered with fine minute hairs.

*Leaf color*.—Spring and fall; upper and lower surface; variegated, margins a blend of N158A and 155A, and centers 143A, summer; upper and lower surface variegated, margins NN155C and lightly tinged with 65D, centers a blend of 143A and 144A, new growth; margins 151C, centers N144A.

*Leaf size*.—Average of 2 cm in length and 1.2 mm in width.

Flower description: Flower production is very rare and no plants with blooms have been available for data collection.

It is claimed:

1. A new and distinct variety of *Sedum* plant named 'Spiraling Doozie' as described and illustrated herein.

* * * * *